(12) United States Patent
Pan

(10) Patent No.: US 8,518,921 B2
(45) Date of Patent: Aug. 27, 2013

(54) COMPOSITIONS AND METHODS FOR INDUCING BONE GROWTH AND INHIBITING BONE LOSS

(75) Inventor: Yuanlong Pan, Chesterfield, MO (US)

(73) Assignee: Nestec SA, Vevey (CH)

( * ) Notice: Subject to any disclaimer, the term of this patent is extended or adjusted under 35 U.S.C. 154(b) by 0 days.

(21) Appl. No.: 13/539,591

(22) Filed: Jul. 2, 2012

(65) Prior Publication Data
US 2012/0277300 A1    Nov. 1, 2012

Related U.S. Application Data

(62) Division of application No. 12/223,431, filed as application No. PCT/US2007/004747 on Feb. 22, 2007, now Pat. No. 8,242,100.

(60) Provisional application No. 60/777,666, filed on Feb. 28, 2006.

(51) Int. Cl.
*A61K 31/56* (2006.01)
*A61K 31/35* (2006.01)

(52) U.S. Cl.
USPC .................. 514/177; 514/178; 514/456

(58) Field of Classification Search
USPC .................................. 514/177, 178, 456
See application file for complete search history.

(56) References Cited

U.S. PATENT DOCUMENTS

2002/0146463 A1* 10/2002 Clayton ................. 424/617

* cited by examiner

*Primary Examiner* — Raymond Henley, III
(74) *Attorney, Agent, or Firm* — Julie M. Lappin; Janet E. Reed

(57) ABSTRACT

Compositions useful for inducing bone growth or inhibiting bone loss in an animal comprising one or more isoflavones or isoflavone metabolites and methods for inducing bone growth or inhibiting bone loss in an animal utilizing such compositions. The compositions and methods are particularly useful for post-menopause, post-andropause, gonadectomized, spayed, or neutered animals.

16 Claims, No Drawings

COMPOSITIONS AND METHODS FOR INDUCING BONE GROWTH AND INHIBITING BONE LOSS

CROSS-REFERENCE TO RELATED APPLICATIONS

This application is a divisional of U.S. patent application Ser. No. 12/223,431 filed Jul. 30, 2008 now U.S. Pat. No. 8,242,100, which is a national stage application under 35 U.S.C. §371 of PCT/US2007/004747 filed Feb. 22, 2007, which claims priority to U.S. Provisional Application Ser. No. 60/777,666 filed Feb. 28, 2006, the disclosures of which are incorporated herein by reference.

BACKGROUND OF THE INVENTION

1. Field of the Invention

The invention relates generally compositions and methods for inducing bone growth or inhibiting bone loss and particularly to the use of isoflavones or metabolites thereof to induce bone growth or to inhibit bone loss.

2. Description of the Related Art

Bone remodeling is a continuing cycle. The cycle begins with osteoclast-mediated bone resorption and is followed by bone mass restoration by osteoblasts. The process of bone remodeling is primarily regulated by sex hormones, especially estrogen. However, genetic, nutritional, and environmental factors can influence bone turnover. Estrogen has been shown to plays a major role in bone remodeling in males as well as females. Estrogen reduces bone remodeling by suppressing osteoclastogenesis and osteoblastogenesis from marrow precursors, inhibits bone resorption by reducing pro-resorptive cytokines, and regulates the lifespan and activities of osteoblasts.

Dysregulation of the bone remodeling cycle often occurs. A more rapid rate of bone tissue dissolution and loss than bone tissue restoration is commonly observed among the aged population. Pathological bone loss is termed osteoporosis. Accelerated bone loss and osteoporosis disproportionately affects females. It is well accepted that estrogen deficiency, brought on by the onset of menopause in females, is a primary contributor to such bone loss. Nevertheless, bone loss and osteoporosis are observed in males.

Although there is no physiological equivalent to menopause in males, many males do experience an age-associated decrease in sex hormone circulation and hypogonadism. These changes are referred to as andropause. Hypogonadism and a decrease in estrogen contribute to bone loss and osteoporosis in males. Thus, both menopause and andropause are risk factors for bone loss.

In addition to menopause and andropause, surgical removal of sex organs affects the levels of sex hormones such as estrogen. Such removal can affect bone size, mass, and density. In animals, procedures such as neutering, spaying, ovariectomy, castration, and the like, are frequently performed for population control. The practical effect of a gonadectomy in mature female animals is the surgical equivalent of naturally occurring menopause in aged female animals because the procedure effectively diminishes circulating levels of sex hormones. After menopause, extragonadal biosynthesis of estrogen in female animals depends on the availability of precursor steroids from the adrenal cortex. Extragonadal biosynthesis of estrogen is also important for the normal function of many tissues and systems including bone in the male animals. Circulating testosterone from the testis appears to be the major precursor for extragonadal estrogen biosynthesis. Male animals maintain sufficient concentrations of circulating testosterone throughout life to support extragonadal biosynthesis of estrogen. Therefore, male animals usually do not suffer osteoporosis until very late in life. However, surgical removal of sex organs in mature male animals leads to complete loss of the production of androgen and estrogen by testis. Such removal also results in the loss of the major precursor for extragonadal estrogen biosynthesis that naturally does not occur in male animals.

Bone strength is largely dependent on bone density and bone quality. In humans, if peak bone mass is not reached in childhood and adolescence a risk of osteoporosis later in life arises. Surgical removal of sex organs in immature and growing male and female animals prevents the animals from reaching peak bone mass by reducing the accumulation of bone mineral density and content. As such, a gonadectomy can be considered a risk factor for impaired bone growth and development in young growing animals.

Hormone replacement therapy and dietary supplementation are frequently used to combat the effects of diminished sex hormone circulation on bone remodeling, particularly on bone loss. With respect to dietary supplementation, dietary phytoestrogens may improve bone mass and bone turnover and play a role in osteogenesis. In addition, dietary phytoestrogens are believed to have beneficial effects in slowing or inhibiting bone loss. However, almost all of the studies related to the beneficial effects of phytoestrogens such as soy isoflavones on bones were conducted in either female animals under the conditions of surgically-induced menopause or in postmenopausal women. There is a dearth of data regarding the effects of isoflavones on bone growth in growing animals and in male animals.

Phytoestrogens are chemicals produced by plants that have a similar structure to mammalian estrogens. Phytoestrogens are subdivided into three major classifications, i.e., coumestans, lignans, and isoflavones. The isoflavones have been shown to have positive effects on bone health.

Given the risk of (1) impaired bone growth and development and (2) accelerated bone loss and osteoporosis in animals that are in menopause or andropause or have been gonadectomized, especially when the animals are growing and their skeletal system has not matured yet, there is a need for novel compositions and methods that promote healthy bone growth and that reduce or inhibit bone loss in animals without the risk of dangerous side effects associated with traditional hormone replacement therapy.

SUMMARY OF THE INVENTION

It is, therefore, an object of the present invention to provide compositions and methods for inducing bone growth or inhibiting bone loss.

It is another object of the present invention to provide compositions and methods for inducing bone growth or inhibiting bone loss in a post-menopause, post-andropause, gonadectomized, spayed, or neutered animal.

It is a further object of the invention to provide articles of manufacture in the form of kits that contain combinations of the isoflavones or metabolites thereof of the present invention, food compositions, compounds, and devices that are useful for inducing bone growth or inhibiting bone loss in an animal.

One or more of these other objects are achieved using novel compositions and methods for inducing bone growth or inhibiting bone loss. Generally, the compositions comprise one or more isoflavones or metabolites thereof in amounts effective for inducing bone growth or inhibiting bone loss.

The isoflavones include at least one of daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, or formononetin. Also, the isoflavones or metabolites thereof are soy isoflavones or metabolites thereof such as equol. The compositions may comprise additional ingredients such as substances that that promote or sustain general healthy bone growth or that inhibit bone loss such as DT56a, androstenedione, dehydroepiandrosterone (DHEA), silicon, conjugated linoleic acid (CLA), or orthosilicic acid.

Other and further objects, features, and advantages of the present invention will be readily apparent to those skilled in the art.

DETAILED DESCRIPTION OF THE INVENTION

Definitions

The following abbreviations may be used herein: CLA, conjugated linoleic acid; BCS, body condition score; BMR, basal metabolic rate; MER, maintenance energy requirement; DEXA, dual energy x-ray absorptiometry; BMC, bone mineral content; BMD, bone mineral density; BW, body weight; SGM; and soy germ meal.

The term "animal" means a human or other animal, including avian, bovine, canine, equine, feline, hicrine, murine, ovine, and porcine animals, that could benefit from inducing bone growth or inhibiting bone loss.

The term "bone affecting agents" means any means any compound, composition, or drug useful for inducing bone growth or inhibiting bone loss in an animal other than the isoflavones or metabolites thereof of the present invention, e.g., bisphosophonates, raloxifene, estrogen, calcitonin, risedronate, and alendronate.

The term "bone growth" means any increase in bone cells or tissue, increase in bone mass, increase of bone minerals, increase of bone density, increase in bone length, or increase in bone width, as measured by any means suitable in the art.

The term "bone loss" means any decrease in bone cells or tissue, decrease in bone mass, decrease of bone minerals, or decrease of bone density in a subject, as measured by any means suitable in the art.

The term "conjugated linoleic" or "CLA" is a collective term used to designate a mixture of positional and geometric isomers of the essential (n-6) fatty acid linoleic acid.

The term "companion animal" means any domesticated animal, including, without limitation, cats, dogs, rabbits, guinea pigs, ferrets, hamsters, mice, gerbils, horses, cows, goats, sheep, donkeys, pigs, and the like.

The term "complete and nutritionally balanced pet food" means a pet food that contains all known required nutrients in appropriate amounts and proportions based on recommendations of recognized authorities in the field of companion animal nutrition and is therefore capable of serving as a sole source of dietary intake to maintain life or promote production without the addition of supplemental nutritional sources. Nutritionally balanced pet food compositions are widely known and widely used in the art.

The term "dietary supplement" means a product that is intended to be ingested in addition to the normal diet of an animal.

The term "effective amount" means an amount of a compound, material, composition, and/or dosage form as described herein that may be effective to achieve a particular biological result. Such results may include, but are not limited to, inducing healthy bone growth in young, growing gonadectomized animals, and inhibiting bone loss in adult animals that are post-menopause or post-andropause or that have been gonadectomized. Such effective activity may be achieved, for example, by causing the ingestion of compositions of the present invention.

The term "gonadectomized" means an animal that has had its generative organs (testis or ovaries) surgically removed.

The term "human food composition" means any composition intended for ingestion by a human.

The term "in conjunction" means that a isoflavones or metabolites thereof, food composition, bone affecting agents, or other compound or composition of the present invention are administered to an animal (1) together in a food composition or (2) separately at the same or different frequency using the same or different administration routes at about the same time or periodically. "Periodically" means that the agent is administered on a dosage schedule acceptable for a specific agent and that the food is fed to an animal routinely as appropriate for the particular animal. "About the same time" generally means that the food and agent are administered at the same time or within about 72 hours of each other. "In conjunction" specifically includes administration schemes wherein bone affecting agents is administered for a prescribed period and the compositions comprising one or more isoflavones or metabolites thereof are administered indefinitely.

The term "isoflavones" means 3-phenylchromones, isomeric forms of flavones in which the benzene group is attached to the 3 position of the benzopyran ring instead of the 2 position, and their respective metabolites. Whenever the term "isoflavones" is used herein, it is intended to encompass derivatives and metabolites of isoflavones, with particular examples of isoflavone derivatives as described herein. Isoflavones may be found in a number of sources, including, but not limited to, soy. Non-limiting examples of isoflavones include daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, formononetin, or any metabolites of isoflavones. Isoflavones and their use for various health benefits are known. For example, soy has been found to reduce the risk of cardiovascular disease; reduce the risk of breast and prostate cancer; relieve hot flushes associated with menopause estrogen deficiency; retard osteoporosis in postmenopause women; reduce total amount of cholesterol, LDL cholesterol, and triglycerides in plasma; preserve cognitive functions in postmenopause women; improve symptoms of hypertension; and promote weight loss.

The term "L-carnitine" means a trimethylammonium (betaine) derivative of $\gamma$-amino-$\beta$-hydroxybutyric acid, formed from N8,N8,N8-trimethyllysine and from $\gamma$-butyrobetaine. L-carnitine is an acyl carrier for the mitochondrial membrane that stimulates fatty acid oxidation. It is sometimes referred to as Vitamin Bt or Vitamin B7.

The term "neutered" means an animal lacking or having imperfectly developed or nonfunctional generative organs, whether such condition occurs congenitally, by natural development processes, or through intervening surgery.

The term "oral administration" or "orally administering" means that an animal orally ingests a food or other composition.

The term "pet food" or "pet food composition" means a composition that is intended for ingestion by an animal, and preferably by companion animals.

The term "single package" means that the components of a kit are physically associated in or with one or more containers and considered a unit for manufacture, distribution, sale, or use. Containers include, but are not limited to, bags, boxes, bottles, shrink wrap packages, stapled or otherwise affixed components, or combinations thereof. A single package may be containers of individual food compositions physically associated such that they are considered a unit for manufacture, distribution, sale, or use.

The term "spay" means the removal of the ovaries of a female animal.

The term "virtual package" means that the components of a kit are associated by directions on one or more physical or virtual kit components instructing the user how to obtain the other components, e.g., in a bag containing one component and directions instructing the user to go to a website, contact a recorded message, view a visual message, or contact a caregiver or instructor to obtain instructions on how to use the kit.

All percentages expressed herein are by weight of the composition on dry matter basis unless specifically stated otherwise. The term "dry matter basis" means that an ingredient's concentration in a composition is measured after any moisture in the composition is removed.

As used throughout, ranges are used for describing each and every value within the range. Any appropriate value within the range can be selected as the upper or lower value for the range.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise. Similarly, the words "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, is relevant prior art for the present invention and the right to challenge the accuracy and pertinence of such patents, patent applications, publications, and other references is specifically reserved.

The Invention

In one aspect, the present invention provides compositions suitable for inducing bone growth or inhibiting bone loss in an animal. The compositions comprise one or more isoflavones or metabolites thereof in an amount effective to induce bone growth or to inhibit bone loss in an animal. The invention is based upon the discovery that isoflavones and various metabolites thereof are effective for promoting healthy bone growth and development and for inhibiting bone loss in animals. The invention is useful for promoting healthy bone growth in young, growing animals and reducing bone loss in mature animals. The compositions have been found particularly effective for inducing bone growth or inhibiting bone loss in a post-menopause, post-andropause, gonadectomized, spayed, or neutered animal, especially when the animal's skeletal system is still growing or maturing.

The isoflavones or metabolites thereof can be present in the composition as an ingredient or additive. In one embodiment, the isoflavones are soy isoflavones. In another, the isoflavones are daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, or formononetin, or metabolites thereof. In a preferred embodiment, the isoflavones metabolite is dihydrodaidzein or equol. In one embodiment, the compositions further comprise L-carnitine and/or conjugated linoleic acid.

In one embodiment, the compositions are pet food compositions. Such compositions include foods intended to supply the necessary dietary requirements for an animal, animal treats (e.g., biscuits), or dietary supplements. The compositions may be a dry composition (e.g., kibble), semi-moist composition, wet composition, or any mixture thereof. In another embodiment, the composition is a dietary supplement such as a gravy, drinking water, beverage, yogurt, powder, granule, paste, suspension, chew, morsel, treat, snack, pellet, pill, capsule, tablet, or any other suitable delivery form. The dietary supplement can comprise a high concentration of isoflavones or metabolites thereof such that the supplement can be administered to the animal in small amounts, or in the alternative, can be diluted before administration to an animal. The dietary supplement may require admixing with water prior to administration to the animal.

The composition may be refrigerated or frozen. The isoflavones or metabolites thereof may be pre-blended with the other components of the composition to provide the beneficial amounts needed, may be coated onto a pet food composition, or may be added to the composition prior to offering it to the animal, e.g., using a sprinkled powder or a mix.

In one embodiment, the compositions of the invention comprise isoflavones or metabolites thereof in an amount effective to induce bone growth in an animal. In another, the compositions comprise isoflavones or metabolites thereof in an amount effective to inhibit bone loss in an animal. Preferably, in these embodiments, the composition comprises from about 0.1% to about 100% isoflavones or metabolites thereof, most preferably from about 0.1% to about 50%. For food compositions, the composition preferably comprises from 0.01% to about 50%, preferably about 0.01% to about 30%. In various embodiments, the composition comprises about 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30%, 40%, 50%, or more of the composition. For example, dietary supplements may be formulated to contain several-fold or more higher concentrations of isoflavones or metabolites thereof than typical compositions such that the supplements are amenable for administration to an animal in the form of a tablet, capsule, liquid concentrated, or other similar dosage form, or to be diluted before administrations, such as by dilution in water, spraying or sprinkling onto a pet food, and other similar modes of administration. Such supplements may comprise 100% isoflavones or metabolites but are often formulated with carriers, excipients, and the like.

The sources of each of the isoflavones or metabolites thereof can be any suitable source, synthetic or natural. Preferred sources of isoflavones include any isoflavones-containing plant, plant material, or plant extract, such as, but not limited to, legumes, clovers, and kudzu root. Preferred legume sources of isoflavones include chick peas, lentils, soy beans, or any other type of beans or peas that contain isoflavones. Soybean meal, soygerm meal, and the like may also be used. Preferred clover sources of isoflavones include red clover and subterranean clover. Alternatively, the isoflavones or metabolites thereof may be synthesized de novo according to any means suitable in the art.

L-carnitine is a naturally occurring compound that plays an important role in energy production in an animal's body. Higher concentrations of L-carnitine are found in tissues that use fatty acid as their primary energy source, such as skeletal and cardiac muscle, compared to other tissues. L-carnitine can stimulate osteoblast differentiation and may play a role in suppressing bone loss. The source for L-carnitine can be any animal tissue, including tissue isolated from mammals, fish, birds, and the like. Similarly, L-carnitine may be obtained from milk isolated from any mammal. Alternatively, L-carnitine can be synthesized de novo according to any means suitable in the art.

CLA plays a role in bone remodeling and growth. In addition, CLA has been shown to benefit BMD in postmenopausal women. The source for CLA can be any animal tissue, including tissue isolated from mammals, bird, fish, and the like. Similarly, CLA can be obtained from milk isolated from any mammal. CLA can also be obtained from plants or plant oils such as sunflower oil. Alternatively, CLA can be synthesized de novo according to any means suitable in the art. CLA may also be derived from synthetic isomers or synthetic analogs of CLA. The compositions may further comprise bone affecting agents in amounts effective for inducing bone growth or inhibiting bone loss in an animal, alone or in combination with the isoflavones or metabolites thereof of the present invention.

In various embodiments, the animal is a human or companion animal such as a post-menopause, post-andropause, gonadectomized, spayed, or neutered animal. In others, the animal is a young or growing animal in which bone development is occurring.

The compositions can optionally comprise supplementary substances such as minerals, vitamins, salts, condiments, colorants, and preservatives. Non-limiting examples of supplementary minerals include calcium, phosphorous, potassium, sodium, iron, chloride, boron, copper, zinc, manganese, iodine, selenium and the like. Non-limiting examples of supplementary vitamins include vitamin A, various B vitamins, vitamin C, vitamin D, vitamin E, and vitamin K. Additional dietary supplements may also be included, for example, niacin, pantothenic acid, inulin, folic acid, biotin, amino acids, and the like.

The compositions can optionally comprise one or more supplementary substances that promote or sustain general healthy bone growth, or that inhibit bone loss. Such substances include, without limitation, DT56a, androstenedione, dehydroepiandrosterone (DHEA), silicon, CLA, and ortho-silicic acid.

In various embodiments, pet food or pet treat compositions comprise from about 15% to about 50% crude protein. The crude protein material may comprise vegetable proteins such as soybean meal, soy protein concentrate, corn gluten meal, wheat gluten, cottonseed, and peanut meal, or animal proteins such as casein, albumin, and meat protein. Non-limiting examples of meat protein useful herein include pork, lamb, equine, poultry, fish, and mixtures thereof.

The compositions may further comprise from about 5% to about 40% fat. The compositions may further comprise a source of carbohydrate. The compositions may comprise from about 15% to about 60% carbohydrate. Non-limiting examples of such carbohydrates include grains or cereals such as rice, corn, milo, sorghum, alfalfa, barley, soybeans, canola, oats, wheat, and mixtures thereof The compositions may also optionally comprise other materials such as dried whey and other dairy by-products.

The compositions may also comprise at least one fiber source. A variety of soluble or insoluble fibers may be utilized, as will be known to those of ordinary skill in the art. The fiber source can be beet pulp (from sugar beet), gum arabic, gum talha, psyllium, rice bran, carob bean gum, citrus pulp, pectin, fructooligosaccharide additional to the short chain oligofructose, mannanoligofructose, soy fiber, arabinogalactan, galactooligosaccharide, arabinoxylan, or mixtures thereof. Alternatively, the fiber source can be a fermentable fiber. Fermentable fiber has previously been described to provide a benefit to the immune system of a companion animal. Fermentable fiber or other compositions known to those of skill in the art which provide a prebiotic composition to enhance the growth of probiotic microorganisms within the intestine may also be incorporated into the composition to aid in the enhancement of the benefit provided by the present invention to the immune system of an animal. Additionally, probiotic microorganisms, such as *Enterococcus, Lactobacillus, Bifidobacterium,* or *Saccharomyces* species, for example, may be added to the composition.

In a preferred embodiment, the composition is a complete and nutritionally balanced pet food. In this embodiment, the pet food may be a wet food, a dry food, or a food of intermediate moisture content, as would be recognized by those skilled in the art of pet food formulation and manufacturing. "Wet food" describes pet food that is typically sold in cans or foil bags, and has a moisture content typically in the range of about 70% to about 90%. "Dry food" describes pet food which is of a similar composition to wet food, but contains a limited moisture content, typically in the range of about 5% to about 15%, and therefore is presented, for example, as small biscuit-like kibbles. The compositions and dietary supplements may be specially formulated for adult animals, or for older or young animals, for example, a "puppy chow," "kitten chow," or "senior" formulation. In general, specialized formulations will comprise energy and nutritional requirements appropriate for animals at different stages of development or age.

Certain aspects of the invention are preferably used in combination with a complete and balanced food. That is, compositions comprising isoflavones or metabolites thereof according to certain embodiments of the invention are preferably used with a high-quality commercial food. As used herein, "high-quality commercial food" refers to a diet manufactured to produce the digestibility of the key nutrients of 80% or more, as set forth in, for example, the recommendations of the National Research Council above for dogs, or in the guidelines set forth by the Association of American Feed Control Officials. Similar high nutrient standards would be used for other animals.

The skilled artisan will understand how to determine the appropriate amount of isoflavones or metabolites thereof to be added to a given composition. Such factors that may be taken into account include the type of composition (e.g., pet food composition versus dietary supplement), the average consumption of specific types of compositions by different animals, and the manufacturing conditions under which the composition is prepared. Preferably, the concentrations of isoflavones or metabolites thereof to be added to the composition are calculated on the basis of the energy and nutrient requirements of the animal. According to certain aspects of the invention, the isoflavones or metabolites thereof can be added at any time during the manufacture and/or processing of the composition. This includes, without limitation, as part of the formulation of the pet food composition or dietary supplement, or as a coating applied to the pet food composition or dietary supplement. The compositions can be made according to any method suitable in the art.

In another aspect, the present invention provides methods for inducing bone growth or inhibiting bone loss in an animal. The methods comprise administering to an animal one or more isoflavones or metabolites thereof in an amount effective to induce bone growth or to inhibit bone loss in the animal. In various embodiments, the isoflavones are daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, or formononetin, or metabolites thereof. In one embodiment, the isoflavones metabolite is dihydrodaidzein or equol. In one embodiment, the compositions further comprise L-carnitine and/or conjugated linoleic acid.

In various embodiments, the composition is a human food composition, pet food composition, or a dietary supplement as described herein. In various embodiments, the isoflavones are daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, or formononetin, or metabolites thereof. In one embodiment, the isoflavones metabolite is dihydrodaidzein or equol. In one embodiment, the methods further comprise administering L-carnitine and/or conjugated linoleic acid in combination with the isoflavones or metabolites thereof. In another, the methods further comprise administering isoflavones or metabolites thereof in conjunction with bone affecting agents in amounts effective for inducing bone growth or inhibiting bone loss in an animal.

In various embodiments, the animal is a human or companion animal such as a dog or cat. In certain embodiments, the animal is a post-menopause, post-andropause, or gonadectomized animal. In others, the animal is a young or growing animal.

The isoflavones or metabolites thereof are administered to the animal using a variety of routes of administration. Such routes include, without limitation, oral, intranasal, intravenous, intramuscular, intragastric, transpyloric, subcutaneous, rectal, and the like. Preferably, the compositions are administered orally.

Administration can be on an as-needed or as-desired basis, for example, once-monthly, once-weekly, daily, or more than once daily. Similarly, administration can be every other day, week, or month, every third day, week, or month, every fourth day, week, or month, and the like. Administration can be multiple times per day. When utilized as a supplement to ordinary dietetic requirements, the composition may be administered directly to the animal or otherwise contacted with or admixed with daily feed or food. When utilized as a daily feed or food, administration will be well known to those of ordinary skill.

Administration can also be carried out as part of a dietary regimen for the animal. For example, a dietary regimen may comprise causing the regular ingestion by the animal of a composition comprising one or more isoflavones or metabolites thereof, in an amount effective to induce bone growth in the animal, or in an amount effective to inhibit bone loss in the animal. Regular ingestion can be once a day, or two, three, four, or more times per day, on a daily basis. The goal of regular ingestion is to provide the animal with the preferred daily dose of isoflavones or metabolites thereof, as exemplified herein.

Preferred daily does ranges for isoflavones and/or metabolites thereof ranges from about 5 mg/day to about 5000 mg/day per animal. Preferably, the daily dose of isoflavones and/or metabolites thereof ranges from about 30 mg/day to about 500 mg/day per animal, and more preferably from about 80 mg/day to about 300 mg/day per animal. The daily dose of isoflavones or metabolites thereof can be measured in terms of grams of isoflavones or metabolites thereof per kg of BW of the animal. The daily dose of isoflavones or metabolites thereof can range from about 0.001 g/kg to about 50 g/kg BW of the animal, although greater or lesser doses can be provided. Preferably, the daily dose of isoflavones or metabolites thereof is from about 0.001 g/kg to about 25 g/kg BW of the animal. More preferably, the daily dose of isoflavones or metabolites thereof is from about 0.001 g/kg to about 10 g/kg BW of the animal. More preferably, the daily dose of isoflavones or metabolites thereof is from about 0.001 g/kg to about 5 g/kg BW of the animal. More preferably, the daily dose of isoflavones or metabolites thereof is from about 0.001 g/kg to about 1 g/kg BW of the animal. More preferably, the daily dose of the isoflavones or metabolites thereof is from about 0.001 g/kg to about 0.15 g/kg BW of the animal.

Preferred daily does ranges for L-carnitine ranges from about 50 mg/day to about 5000 mg/day per animal. Preferably, the daily dose of L-carnitine ranges from about 80 mg/day to about 500 mg/day per animal, and more preferably from about 100 mg/day to about 300 mg/day per animal. The daily dose of L-carnitine can be measured in terms of grams of L-carnitine per kg of BW of the animal. The daily dose of L-carnitine can range from about 0.001 g/kg to about 50 g/kg BW of the animal, although greater or lesser doses can be provided. Preferably, the daily dose of L-carnitine is from about 0.001 g/kg to about 25 g/kg BW of the animal. More preferably, the daily dose of L-carnitine is from about 0.001 g/kg to about 10 g/kg BW of the animal. More preferably, the daily dose L-carnitine is from about 0.001 g/kg to about 5 g/kg BW of the animal. More preferably, the daily dose of L-carnitine is from about 0.001 g/kg to about 1 g/kg BW of the animal. Preferred daily does ranges for CLA ranges from about 50 mg/day to about 10,000 mg/day per animal. Preferably, the daily dose of CLA ranges from about 500 mg/day to about 6000 mg/day per animal, and more preferably from about 1000 mg/day to about 4000 mg/day per animal.

The daily dose of CLA can be measured in terms of grams of CLA per kg of BW of the animal. The daily dose of CLA can range from about 0.001 g/kg to about 50 g/kg BW of the animal, although greater or lesser doses can be provided. Preferably, the daily dose of CLA is from about 0.001 g/kg to about 25 g/kg BW of the animal. More preferably, the daily dose of CLA is from about 0.001 g/kg to about 10 g/kg BW of the animal. More preferably, the daily dose CLA is from about 0.001 g/kg to about 5 g/kg BW of the animal. More preferably, the daily dose of CLA is from about 0.001 g/kg to about 1 g/kg BW of the animal.

When formulating the compositions of the present invention, a skilled can determine the amounts of the isoflavones or metabolites thereof and other compounds or ingredients based upon the dosages above and the characteristics of the animal. e.g., the animal's species, age, size, weight, health, and the like.

According to the methods of the invention, administration of the isoflavones or metabolites thereof, including administration as part of a diet regimen, can span a period of time ranging from parturition through the adult life of the animal.

In a further aspect, the present invention provides kits suitable for administering a composition comprising one or more isoflavones or metabolites thereof to an animal. The kits comprise in separate containers in a single package or in separate containers in a virtual package, as appropriate for the kit component, one or more isoflavones or metabolites thereof and at least one of (1) one or more ingredients suitable for consumption by an animal, (2) one or more bone affecting agents suitable for inducing bone growth or inhibiting bone loss, (3) instructions for how to combine the isoflavones or metabolites thereof and other kit components, particularly to produce a food composition useful for administering isoflavones or metabolites thereof to an animal, and (4) instructions for how to use the isoflavones or metabolites thereof and other components of the present invention, particularly for the benefit of the animal by inducing bone growth or inhibiting bone loss in the animal.

When the kit comprises a virtual package, the kit is limited to instructions in a virtual environment in combination with one or more physical kit components. The kit contains the isoflavones or metabolites thereof and other components in an amount effective to induce bone growth or inhibit bone loss in the animal. Typically, the isoflavones or metabolites thereof and the other suitable kit components (e.g., food compositions) are admixed just prior to consumption by an animal. The kits may contain the kit components in any of various combinations and/or mixtures. In one embodiment, the kit contains a packet containing one or more of the isoflavones or metabolites thereof and a container of food for consumption by an animal. The kit may contain additional items such as a device for mixing the isoflavones or metabolites thereof and ingredients or a device for containing the admixture, e.g., a food bowl. In another embodiment, the isoflavones or metabolites thereof are mixed with additional nutritional supplements such as vitamins and minerals that promote good health in an animal.

The instructions can direct and/or inform a consumer, doctor, pet owner, veterinarian, food supplier, and the like that use of the isoflavones or metabolites thereof can be used to induce bone growth or to inhibit bone loss in an animal. The instructions can also direct the user how to apply or admix the isoflavones or metabolites thereof to the food or water of an animal.

In another aspect, the present invention provides a means for communicating information about or instructions for one or more of (1) using the isoflavones or metabolites thereof to induce bone growth or to inhibit bone loss in an animal, (2) admixing the isoflavones or metabolites thereof with the other components (food compositions) of the present invention, (3) administering the isoflavones or metabolites thereof to an animal, alone or in combination with the other elements of the present invention, and (4) using the kits of the present invention to administer isoflavones or metabolites thereof to an animal, particularly to induce bone growth or to inhibit bone loss in an animal. The means comprises a document, digital storage media, optical storage media, audio presentation, or visual display containing the information or instructions. In certain embodiments, the communication means is a displayed web site, visual display kiosk, brochure, product label, package insert, advertisement, handout, public announcement, audiotape, videotape, DVD, CD-ROM, computer readable chip, computer readable card, computer readable disk, computer memory, or combination thereof containing such information or instructions. Useful information includes one or more of (1) methods and techniques for combining and administering the isoflavones or metabolites thereof and/or other components and (2) contact information for animals or their caregivers to use if they have a question about the invention and its use. Useful instructions include amounts for mixing and administration amounts and frequency. The communication means is useful for instructing on the benefits of using the present invention and communicating the approved methods for administering the invention to an animal.

In another aspect, the present invention provides a method for manufacturing a food composition containing isoflavones or metabolites thereof comprising admixing one or more ingredients suitable for consumption by an animal and isoflavones or metabolites thereof or applying isoflavones or metabolites thereof onto the food composition. In a further aspect, the present invention provides the food compositions manufactured using this method.

In a further aspect, the present invention provides for a use of isoflavones or metabolites thereof to prepare a medicament. In another, the invention provides for the use of such isoflavones or metabolites thereof to prepare a medicament for to inducing bone growth or inhibiting bone loss in an animal. Generally, medicaments are prepared by admixing a compound or composition with excipients, buffers, binders, plasticizers, colorants, diluents, compressing agents, lubricants, flavorants, moistening agents, and other ingredients known to skilled artisans to be useful for producing medicaments and formulating medicaments that are suitable for administration to an animal.

EXAMPLES

The invention can be further illustrated by the following examples, although it will be understood that these examples are included merely for purposes of illustration and are not intended to limit the scope of the invention unless otherwise specifically indicated.

Example 1

Effect of Dietary Soy Isoflavones on Bone Growth in Normal, Gonadectomized Dogs

Dogs and Diets: Thirty normal, non-obese, newly gonadectomized Labrador Retrievers, 4-5 months old, were used in the study. Puppies were randomized into three groups based on littermates to minimize genetic influence on skeletal muscle growth and health: Group 1 consisted of ten newly gonadectomized male and female Labrador Retrievers, which were fed a well-balanced puppy diet comprising 29 to 30% protein and 20% fat (the control diet). Group 2 consisted of ten newly gonadectomized male and female Labrador Retrievers, which were fed the control diet supplemented with 10% soy germ meal (SGM). Group 3 consisted of ten newly gonadectomized male and female Labrador Retrievers, which were fed the control diet supplemented with 10% SGM, 100 ppm L-carnitine, and 1.5% CLA. SGM contains the following soy isoflavones: 17% genistein, 52% daidzein, and 31% glycitein. All puppies were fed to maintain their ideal body condition score, 5, by adjusting their food intakes. The duration of the study was 70 weeks.

All dogs were given a pre-study MER determination. Before the study, and every week after the study began through the conclusion of the study, the BW was measured made for each animal. Before the study, and bimonthly after the study began through the conclusion of the study, the following measurements were taken for each animal: DEXA for body fat, lean body mass, bone chemistry, expanded thyroid profile, complete blood count, BMC, lumbar spine bone mineral content, and lumbar spine bone mineral density.

After 70-weeks of growth study, no differences in BW, lean body mass, or body fat was observed among three groups. All parameters measured in blood chemistry, expanded thyroid profile, and complete blood count were also determined to be within the normal range. Results related to skeletal growth are shown in Tables 1-4. BMC and BMD were assessed on lumbar spines 1-7 of each puppy in each experimental group.

The results are shown in Tables 1 through 4. Generally, the Tables show the effects of isoflavones on BMC and BMD. Puppies were fed a control diet (Ration 1), with 29 to 30% protein and 20% fat, an Isoflavone diet (Ration 2) (control diet supplemented with 10% SGM), or a Cocktail diet (Ration 3) (control diet supplemented with 10% SGM, 100 ppm L-carnitine, and 1.5% CLA. In the Tables, Ration 1=control, Ration 2=isoflavones, Ration 3=isoflavones, CLA and L-carnitine.

Referring to the Tables, Table 1 shows the effects of dietary soy isoflavones on the BMC of lumbar spines 1-4 in gonadectomized growing male and female puppies (4 months old) during a 70-week growth study. Puppies were fed to maintain their ideal body condition score of 5 by adjusting their food intakes. Referring to the results, BMC increased in control dogs over the 70 week study, but the BMC in puppies consuming the isoflavone or isoflavone-containing cocktail diets was found to be higher than the BMC in puppies consuming the control diet at almost all times tested and at the end of the study. These data clearly indicate that existing well-balanced, high quality puppy diet failed to promote an optimal increase in BMC in gonadectomized, growing male and female puppies.

Table 2 shows changes in BMD of lumbar spines 1-4 in the gonadectomized growing male and female puppies (4 months old) during the 70-week growth study. Referring to the results, BMD of lumbar spines 1-4 increased in the control dogs over the course of the 70 week study, but dogs consuming the isoflavone or isoflavone-containing cocktail diets had a higher BMD than the control dogs. These data show that existing well-balanced, high quality puppy diet failed to promote an optimal increase in BMD in gonadectomized, growing male and female puppies.

Table 3 shows the effects of dietary soy isoflavones on the BMC of lumbar spines 4-7 in gonadectomized growing male and female puppies (4 months old) during the 70-week growth study. Referring to the results, BMC increased in control dogs over the 70 week study, but the BMC in puppies consuming the isoflavone or isoflavone-containing cocktail diets was found to be higher than the BMC in puppies consuming the control diet at the end of the study. Notably, in contrast to the results observed in lumbar spines 1-4, where BMC was generally the same between dogs fed the cocktail and isoflavone diets, the results observed in lumbar spines 4-7 indicate that on the whole, dogs fed the cocktail diet had a higher BMC than dogs fed the isoflavone diet.

Table 4 shows changes in BMD of lumbar spines 4-7 in the gonadectomized growing male and female puppies (4 months old) during the 70-week growth study. Referring to the results, BMD of lumbar spines 4-7 increased in the control dogs over the course of the 70 week study, but dogs consuming the isoflavone or isoflavone-containing cocktail diets had a higher BMD than the control dogs at the end of the study when the skeletal system of the dogs reached maturity. These data show that existing well-balanced, high quality puppies diets could not compensate the loss of growth-promoting effects of estrogen that was lost after gonadectomy. As the results show, the control puppies never achieved optimal peak BMC and BMD when their skeletal system reached maturity. Conversely, isoflavones and the isoflavone-containing cocktail are effective in promoting better bone growth (higher BMC and BMD) in gonadectomized growing puppies.

TABLE 1

|  | Weeks | Ration 1 | SE 1 | Ration 2 | SE 2 | Ration 3 | SE 3 |
| --- | --- | --- | --- | --- | --- | --- | --- |
| L1-L4 BMC | 16 | 13.2741 | 1.1223 | 12.6152 | 1.1223 | 12.8699 | 1.0874 |
| L1-L4 BMC | 26 | 19.0018 | 1.0715 | 18.9969 | 1.0717 | 20.2617 | 1.0348 |
| L1-L4 BMC | 34 | 22.1142 | 1.0637 | 22.6728 | 1.0637 | 23.7819 | 1.0378 |
| L1-L4 BMC | 42 | 24.2471 | 1.0434 | 25.2927 | 1.0435 | 25.7862 | 1.0244 |
| L1-L4 BMC | 50 | 25.7025 | 1.054 | 27.0549 | 1.0545 | 26.8387 | 1.0396 |
| L1-L4 BMC | 58 | 26.7823 | 1.0708 | 28.1578 | 1.0717 | 27.5036 | 1.0601 |
| L1-L4 BMC | 66 | 27.7883 | 1.0656 | 28.7997 | 1.0658 | 28.3452 | 1.0574 |
| L1-L4 BMC | 70 | 28.3579 | 1.1022 | 29.0097 | 1.1022 | 29.0085 | 1.0956 |

TABLE 2

|  | Weeks | Ration 1 | SE 1 | Ration 2 | SE 2 | Ration 3 | SE 3 |
| --- | --- | --- | --- | --- | --- | --- | --- |
| L1-L4 BMD | 16 | 0.7067 | 0.02817 | 0.7049 | 0.02817 | 0.7341 | 0.02722 |
| L1-L4 BMD | 26 | 0.826 | 0.02715 | 0.836 | 0.02715 | 0.8561 | 0.02616 |
| L1-L4 BMD | 34 | 0.8847 | 0.02699 | 0.9072 | 0.02699 | 0.9107 | 0.02624 |
| L1-L4 BMD | 42 | 0.92 | 0.02659 | 0.9543 | 0.02659 | 0.9399 | 0.02599 |
| L1-L4 BMD | 50 | 0.9404 | 0.0268 | 0.9831 | 0.0268 | 0.9555 | 0.02631 |
| L1-L4 BMD | 58 | 0.9542 | 0.02714 | 0.9992 | 0.02714 | 0.9695 | 0.02675 |
| L1-L4 BMD | 66 | 0.9699 | 0.02703 | 1.0081 | 0.02703 | 0.9938 | 0.02673 |
| L1-L4 BMD | 70 | 0.9811 | 0.02776 | 1.0116 | 0.02776 | 1.0135 | 0.0275 |

TABLE 3

|  | Weeks | Ration 1 | SE 1 | Ration 2 | SE 2 | Ration 3 | SE 3 |
|---|---|---|---|---|---|---|---|
| L4-L7 BMC | 16 | 14.4363 | 1.1379 | 13.5979 | 1.1379 | 14.426 | 1.1001 |
| L4-L7 BMC | 26 | 20.7348 | 1.0949 | 20.6968 | 1.0949 | 22.369 | 1.0554 |
| L4-L7 BMC | 34 | 24.4373 | 1.0883 | 24.7872 | 1.0883 | 26.4567 | 1.0585 |
| L4-L7 BMC | 42 | 27.1118 | 1.0711 | 27.693 | 1.0711 | 29.0178 | 1.0476 |
| L4-L7 BMC | 50 | 28.9061 | 1.08 | 29.6245 | 1.08 | 30.5032 | 1.061 |
| L4-L7 BMC | 58 | 29.9677 | 1.0944 | 30.7917 | 1.0944 | 31.3636 | 1.0793 |
| L4-L7 BMC | 66 | 30.4443 | 1.0899 | 31.405 | 1.0899 | 32.0497 | 1.0782 |
| L4-L7 BMC | 70 | 30.5093 | 1.1208 | 31.5695 | 1.1208 | 32.4683 | 1.111 |

TABLE 4

|  | Weeks | Ration 1 | SE 1 | Ration 2 | SE 2 | Ration 3 | SE 3 |
|---|---|---|---|---|---|---|---|
| L4-L7 BMD | 16 | 0.6846 | 0.02579 | 0.6652 | 0.02579 | 0.7117 | 0.02496 |
| L4-L7 BMD | 26 | 0.799 | 0.02473 | 0.8009 | 0.02473 | 0.827 | 0.02385 |
| L4-L7 BMD | 34 | 0.856 | 0.02456 | 0.8643 | 0.02456 | 0.8821 | 0.02392 |
| L4-L7 BMD | 42 | 0.8904 | 0.02414 | 0.9003 | 0.02414 | 0.9145 | 0.02365 |
| L4-L7 BMD | 50 | 0.9099 | 0.02436 | 0.9208 | 0.02436 | 0.9335 | 0.02397 |
| L4-L7 BMD | 58 | 0.9221 | 0.02471 | 0.9376 | 0.02471 | 0.9488 | 0.02441 |
| L4-L7 BMD | 66 | 0.9347 | 0.0246 | 0.9626 | 0.0246 | 0.9697 | 0.02437 |
| L4-L7 BMD | 70 | 0.9434 | 0.02537 | 0.9818 | 0.02537 | 0.9852 | 0.02518 |

In the specification, there have been disclosed typical preferred embodiments of the invention and, although specific terms are employed, they are used in a generic and descriptive sense only and not for purposes of limitation, the scope of the invention being set forth in the claims. Obviously many modifications and variations of the invention are possible in light of the above teachings. It is therefore to be understood that within the scope of the appended claims the invention may be practiced otherwise than as specifically described.

What is claimed is:

1. A composition comprising one or more isoflavones or metabolites thereof in an amount effective to induce bone growth in an animal, further comprising at least one of DT56a, androstenedione, dehydroepiandrosterone (DHEA), silicon, L-carnitine, conjugated linoleic acid, and orthosilicic acid.

2. The composition of claim 1 wherein the composition is a human food composition, pet food composition, or a dietary supplement.

3. The food composition of claim 2 wherein the food composition comprises from about 0.1% to about 50% isoflavones or metabolites thereof.

4. The composition of claim 1 wherein the isoflavones include at least one of daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, or formononetin.

5. The composition of claim 1 wherein the isoflavones or metabolites thereof are soy isoflavones or metabolites thereof.

6. The composition of claim 5 wherein the soy isoflavone metabolite is equol.

7. The composition of claim 1 wherein the animal is a post-menopause, post-andropause, gonadectomized, spayed, or neutered animal.

8. A kit suitable for administering a composition comprising one or more isoflavones or metabolites thereof to an animal comprising in separate containers in a single package or in separate containers in a virtual package, one or more isoflavones or metabolites thereof and at least one of (1) one or more ingredients suitable for consumption by an animal, (2) one or more bone affecting agents selected from DT56a, androstenedione, dehydroepiandrosterone (DHEA), silicon, L-carnitine, conjugated linoleic acid, and orthosilicic acid, (3) instructions for how to combine the isoflavones or metabolites thereof and other kit components, and (4) instructions for how to use the isoflavones or metabolites thereof and other components to induce bone growth in the animal.

9. The composition of claim 1, formulated for administration to a young or growing animal.

10. The composition of claim 9, formulated as a puppy food or kitten food.

11. The kit of claim 8, comprising instructions for how to use the isoflavones or metabolites thereof to induce bone growth in a young or growing animal.

12. The kit of claim 11, wherein the animal is gonadectomized.

13. The kit of claim 12, wherein the animal is a puppy or kitten.

14. A dog or cat food comprising one or more isoflavones or metabolites thereof in an amount effective to induce bone growth in a young or growing dog or cat.

15. The dog or cat food of claim 14, which is a puppy or kitten food.

16. The dog or cat food of claim 14, further comprising one or more components selected from DT56a, androstenedione, dehydroepiandrosterone (DHEA), silicon, L-carnitine, conjugated linoleic acid, and orthosilicic acid.

* * * * *